(12) United States Patent
Peeters et al.

(10) Patent No.: US 10,357,188 B2
(45) Date of Patent: Jul. 23, 2019

(54) FLEXIBLE OPTICAL SOURCE FOR PULSE OXIMETRY

(71) Applicant: KONINKLIJKE PHILIPS N.V., Eindhoven (NL)

(72) Inventors: Wouter Herman Peeters, Eindhoven (NL); Toeno Van Der Sar, Eindhoven (NL); Egbertus Reiner Jacobs, Overloon (NL); Gilbert Martinus Verbeek, Eindhoven (NL); Johannes Wilhelmus Weekamp, Beek en Donk (NL)

(73) Assignee: Koninklijke Philips N.V., Eindhoven (NL)

( * ) Notice: Subject to any disclaimer, the term of this patent is extended or adjusted under 35 U.S.C. 154(b) by 978 days.

(21) Appl. No.: 14/857,957

(22) Filed: Sep. 18, 2015

(65) Prior Publication Data
US 2016/0106352 A1  Apr. 21, 2016

Related U.S. Application Data

(60) Provisional application No. 62/063,981, filed on Oct. 15, 2014.

(51) Int. Cl.
*A61B 5/1455* (2006.01)
*A61B 5/024* (2006.01)
*A61B 5/00* (2006.01)

(52) U.S. Cl.
CPC ...... *A61B 5/14552* (2013.01); *A61B 5/02433* (2013.01); *A61B 5/02438* (2013.01); *A61B 5/6833* (2013.01); *A61B 2560/0412* (2013.01); *A61B 2562/146* (2013.01); *A61B 2562/164* (2013.01)

(58) Field of Classification Search
CPC .............. A61B 5/1455; A61B 5/14551; A61B 2562/0233
See application file for complete search history.

(56) References Cited

U.S. PATENT DOCUMENTS

| | | | |
|---|---|---|---|
| 3,871,747 A | 3/1975 | Andrews | |
| 7,120,481 B2 * | 10/2006 | Keller | ............... A61B 5/14553 600/339 |
| 7,181,096 B2 | 2/2007 | Matsumoto et al. | |
| 8,452,366 B2 | 5/2013 | Gilland | |
| 8,577,435 B2 | 11/2013 | Haisley et al. | |
| 2009/0018452 A1 | 1/2009 | Sugiura et al. | |

(Continued)

OTHER PUBLICATIONS

Agashe, G. S., et al.; Forehead Pulse Oximetry; 2006; Anesthesiology; 105(6)1111-1116.

(Continued)

*Primary Examiner* — Eric F Winakur

(57) ABSTRACT

An optical source for guiding light to a target of a patient includes at least one light source configured to emit red light and infrared light. The at least one light source is embedded within a light-conducting sheet. A photodistributor is spaced from the at least one light source. The photodistributor includes a light-emitting surface and at least one light-receiving surface optically coupled to the light-conducting sheet. The photodistributor is configured to discharge at least a portion of the emitted red light and at least a portion of the emitted infrared light into a target.

18 Claims, 4 Drawing Sheets

(56) References Cited

U.S. PATENT DOCUMENTS

| | | |
|---|---|---|
| 2013/0131519 A1 | 5/2013 | Leboeuf et al. |
| 2014/0005557 A1 | 1/2014 | Rich et al. |
| 2014/0155753 A1 | 6/2014 | McGuire et al. |
| 2014/0249381 A1 | 9/2014 | LeBoeuf et al. |

OTHER PUBLICATIONS

ASA; Standards for Basic Anesthetic Monitoring; 1986; ASA House of Delegates.

Dassel, A. C. M., et al.; Reflectance Pulse Oximetry at the Forehead Improves by Pressure on the Probe; 1995; Journal of Clinical Monitoring and Computing; 11(4)237-244.

Groveman, J., et al.; Rhinoplethysmography Pulse Monitoring at the Nasal Septum; 1966; Anesth. Analg.; 45(1) 63-68.

Mannheimer, P. D., et al.; The Influence of Larger Subcutaneous Blood Vessels on Pulse Oximetry; 2004; Journal of Clinical Monitoring and Computing; 18(3)179-188.

Nijland, R., et al.; The Effect of Pulsating Arteries on Reflectance Pulse Oximetry: Measurements in Adults and Neonates; 1995; J. Clin. Monit; 11:118-122.

Oneal, R. M., et al.; Surgical Anatomy of the Nose; 2010; Clin Plastic Surg; 37:191-211.

Philips Disposable sensors that last; 2009; www.philips.com/healthcare.

Philips Reusable sensors that last; 2008; www.philips.com/healthcare.

Reisner, A., et al.; Utility of the Photoplethysmogram in Circulatory Monitoring; 2008; Anesthesiology; 108(5) 950-958.

Shelley, K. H., et al.; The Effect of Venous Pulsation on the Forehead Pulse Oximeter Wave Form as a Possible Source of Error in Spo2 Calculation; 2005; Anesthesiology; 100:743-747.

Tremper, K. K., et al.; Medical Intelligence Article: Pulse Oximetry; 1989; Anesthesiology; 70:98-108.

Venema, B., et al.; Advances in Reflective Oxygen Saturation Monitoring with a Novel In-Ear Sensor System: Results of a Human Hypoxia Study; 2012; IEEE Trans. on Biomedical Engineering; 59(7)2003-2010.

Webster, J. G.; Design of Pulse Oximeters; 1997; 1st Ed.; New York, NY; Taylor & Francis Group; pp. 1-129.

Yelderman, M.; Real Time Oximetry; 1983; Computing in Anesthesia and Intensive Care; Martinus Nijhoff Pub.; Omar Prakash, ed.; pp. 328-341.

\* cited by examiner

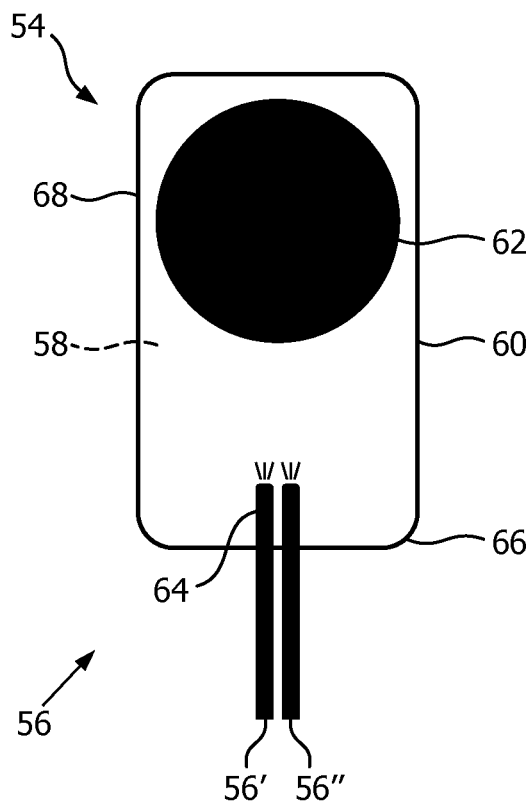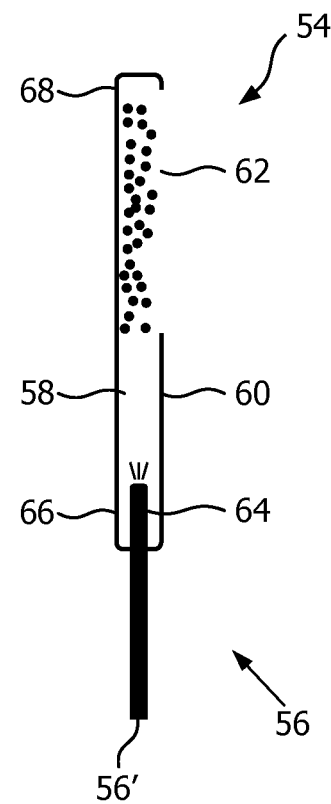
FIG. 5A  FIG. 5B
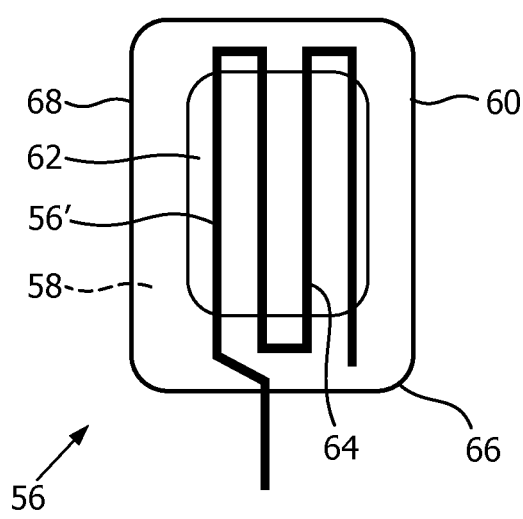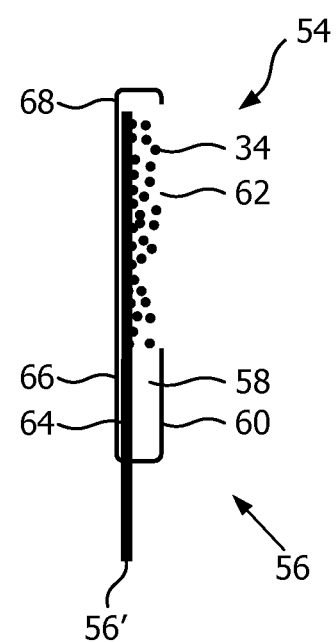
FIG. 5C  FIG. 5D

FLEXIBLE OPTICAL SOURCE FOR PULSE OXIMETRY

CROSS REFERENCE TO RELATED APPLICATIONS

This application claims the benefit of U.S. provisional application Ser. No. 62/063,981 filed Oct. 15, 2014, which is incorporated herein by reference.

The present application relates generally to measuring indications of pulse rate and arterial oxygen saturation ($SpO_2$) of a patient. It finds particular application in conjunction with providing an optical sensor of a pulse oximeter. The optical source includes an enlarged light-emitting outlet while having a low degree of thickness and a high degree of flexibility to allow positioning of the optical source about a target tissue of a patient and will be described with particular reference thereto. However, it is to be understood that it also finds application in other usage scenarios and is not necessarily limited to the aforementioned application.

Pulse oximetry has become a standard of care in clinical practice. It provides a continuous non-invasive readout of critically important information about the patient's pulse rate and $SpO_2$.

In pulse oximetry, red and infrared light is passed through the tissue and is picked up by a light detector. The cardiac pulse rate is derived from a pulsatile light signal that is caused by the pulsating arterial blood volume. A measurement of oxygenation is made based on the ratio of pulse amplitudes at red and infrared signals, based on the difference in color between oxygen-bound hemoglobin and oxygen-unbound hemoglobin.

However, the precision of the measurement technology is limited, which puts restrictions on the available target tissue measurement sites and can cause unreliable readings. There are four important limiting aspects of pulse oximetry: (1) the sensitivity of the SpO2 reading due to the presence of large arteries or an inhomogeneous vascular bed; (2) the bulky size of pulse oximeter probes to fit into narrow spaces inside and on the outside of the human body; (3) the sensitivity of the plethysmographic signal and the SpO2 reading to the contact pressure of the sensor; and (4) the occurrence of discomfort due to prolonged contact pressure points on the tissue.

First, the presence of large arteries in the tissue, or an inhomogeneous vasculature, can significantly reduce the accuracy of pulse oximetry. The exact location of these larger arteries with respect to the source and detector of the pulse oximeter depends very much on sensor placement, and also varies from patient to patient. These factors reduce the accuracy and precision of the pulse oximeter. Current commercial sensors are applied to body parts where no large arteries are present close to the skin surface (e.g., the finger, the ear lobe, the ear conga, the area just above the eye brow, etc.). Areas with large arteries, such as the temple and ear-canal, are not suitable for SpO2 measurements because the presence of the large arteries can disable universal calibration of the pulse oximeter.

Inhomogeneous vasculature limits the use of mucosal tissue for pulse oximetry. Mucosal tissue lacks an epidermis and dermis, which is an optical disadvantage because an epidermis and/or a dermis layer would homogenize the light before it could encounter any thicker blood vessels. A very interesting mucosal site would be the nasal septum because of its persistent perfusion properties in critically weak patients. The presence of larger arteries close to the tissue surface, however, makes the measurement unreliable.

Second, a thin optical source and detector would enable a pulse oximeter to be disposed in a narrow space (e.g., the nostril, the nasal pads of glasses, behind the ear, etc.). For example, the space between the septum and the other side of the nostril can be approximately 2 mm.

Third, the SpO2 measurement is very sensitive to the applied contact force by the sensor to the tissue. The light sensor needs to gently exert a minor level of pressure to remove venous pulsations for a reliable SpO2 measurement. However, patient movement often results in fluctuations of the contact pressure, thereby causing an unreliable measurement. The rigidity of current pulse oximeters induces a strong sensitivity of the contact pressure to motion of the patient. For example, the septum cannot deform easily, while in every patient the septum may have a different curvature or shape. A rigid optical contact would make the measurement highly sensitive to motion.

Fourth, the rigidity of current pulse oximeters causes patient discomfort. Due to the rigidity of the sensor, the tissue of the patient deforms such that it evenly touches the rigid optical sensor regardless of any tissue surface irregularities or curvature. However, prolonged tissue deformation causes discomfort and, in severe cases, tissue necrosis. Also, if the tissue (e.g., the nasal septum) cannot deform because of its stiffness, the contact between the tissue and the sensor will most likely not match well, causing increased pressure contacts and discomfort.

The present application provides new and improved methods and systems which overcome the above-referenced problems and others.

A solution to the large artery problem can be to make the area of the source much larger than the maximum size of the vessels. Blockage of the dominant light path by a large vessel is thereby prevented because the dominant light path is spatially distributed and will always form around any larger vessel. The typical light sources for pulse oximetry (i.e., LEDs), however, are typically much smaller (~100 microns). This problem is solved with a rigid light diffusing material placed in front of the LED to enlarge the spatial region over which light is emitted.

An enlarged area of optical illumination is difficult to combine with the narrow space/cavity tissue since an extra layer of diffusing material induces extra thickness. For example, if the sensor has an optical illumination area with a diameter of 10 mm is desired, an extra layer of 5 mm is needed to achieve this size, thereby limiting the applicability of the sensor in confined spaces on the body. One method to overcome this problem is known in display making, where LEDs are placed on the sides of a planar waveguide and light is scattered out of the waveguide (see U.S. Pat. No. 3,871,747). However, such a waveguide does not work in direct contact with human tissue because human tissue has a higher refractive index than air (i.e. the outcouple medium of displays). Consequently, light is coupled out of the waveguide too quickly, resulting in poor out-coupling of the light into the tissue.

An enlarged area of the optical illumination is also difficult to combine with the inhomogeneous contact pressure issue and the patient discomfort issue. If the rigid optical source area is enlarged, then the degree of tissue deformation will also increase proportionally. If the tissue geometry does not complement the geometry of the sensor, then there is risk of sensitivity to the applied pressure and patient and sensor motion. The sensor will also be much less comfortable due to the inhomogeneously applied pressure.

For example, a solid planar structure pressed against a curved nasal septum will feel highly uncomfortable to the patient.

In accordance with one aspect, an optical source for guiding light to a target of a patient is provided. The optical source includes at least one light source configured to emit red light and infrared light. The at least one light source is embedded within a light-conducting sheet. A photodistributor is spaced from the at least one light source. The photodistributor includes a light-emitting surface and at least one light-receiving surface optically coupled to the light-conducting sheet. The photodistributor is configured to discharge at least a portion of the emitted red light and at least a portion of the emitted infrared light into a target.

In accordance with another aspect, a method for lighting a target with red and infrared light includes positioning an optical source at least adjacent to the target. Each of red light and infrared light is emitted from at least one light source. At least a portion of the red light and at least a portion of the infrared light are guided along a flexible light-conducting sheet. At least a portion of the red light and at least a portion of the infrared light are directed into the target via a flexible light-emitting surface that abuts at least a portion of the target.

In accordance with another aspect, an optical source for guiding light to a target of a patient is provided. The optical source includes at least one light source configured to emit red light and infrared light. A light-conducting sheet is molded around at least a portion of the at least one light source. The light-conducting sheet is configured to guide at least a portion of emitted red light and at least a portion of emitted infrared light. A coating layer is disposed on at least a portion of the light-conducting sheet. The coating layer is configured to reflect at least a portion of the emitted red light and at least a portion of the emitted infrared light and retain the emitted red light and infrared light in the light-conducting sheet. An outlet is disposed on a portion of the light-conducting sheet that is free from engagement with the coating layer. The outlet is surrounded by at least a portion of the coating layer. The outlet is configured to emit red light and infrared light towards a target.

One advantage resides in providing accurate readings of pulse rate and $SpO_2$ in the presence of large arteries and/or inhomogeneous vasculature in a target tissue.

Another advantage resides in placement of a pulse oximeter in a narrow target tissue.

Another advantage resides in placement of a pulse oximeter about a curved target tissue.

Another advantage resides in increased patient comfort.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIGS. 5A-5D are illustrations of an alternate embodiment of an optical source for use with a pulse oximeter.

Figure 1:
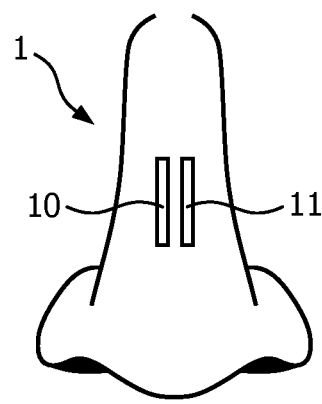
FIG. 1 illustrates an optical source positioned adjacent a target tissue.

The present application is directed to a system and method for an optical source 10 of a pulse oximeter 1. With reference to FIG. 1, the optical source 10 is configured for use with a light-receiving device 11 of the pulse oximeter 1 that is positioned on or adjacent to a target tissue. As used herein, the term "target tissue" refers to any desired target tissue (e.g., the septum, the outside of the nose, inside the nostril, a finger, an ear lobe, an ear conga, behind the ear, inside the ear, an area above the eye brow, in the eye pit, inside the esophagus, the oral mucosal, the skull, on the forehead, etc.). The optical source 10 (and, optionally, the light-receiving device 11) is spatially-extended, thin and flexible. The spatially-extended dimensions of the optical source 10 (and, optionally, the light-receiving device 11) allow the pulse oximeter to obtain accurate readings indicative of a vital sign of a patient (e.g., pulse rate, $SpO_2$, etc.) in the presence of inhomogeneities and large pulsating arteries while decreasing the likelihood of potential displacement during use. The small thickness of the optical source 10 (and, optionally, the light-receiving device 11) to enables pulse oximetry in confined spaces of the target tissue. The flexibility of the optical source 10 enables pulse oximetry on curved target tissues and helps avoid pressure points and discomfort. The flexibility of the optical source 10 (and, optionally, the light-receiving device 11) also ensures homogeneous, minimal pressure contact on every patient to measure $SpO_2$ value. As used herein, the term "flexibility" and variants thereof refers to a characteristic of an element or structure that has a low value of stiffness relative to septum and other tissues against which the optical source 10 (and, optionally, the light-receiving device 11) is configured to be disposed.

Figure 2:
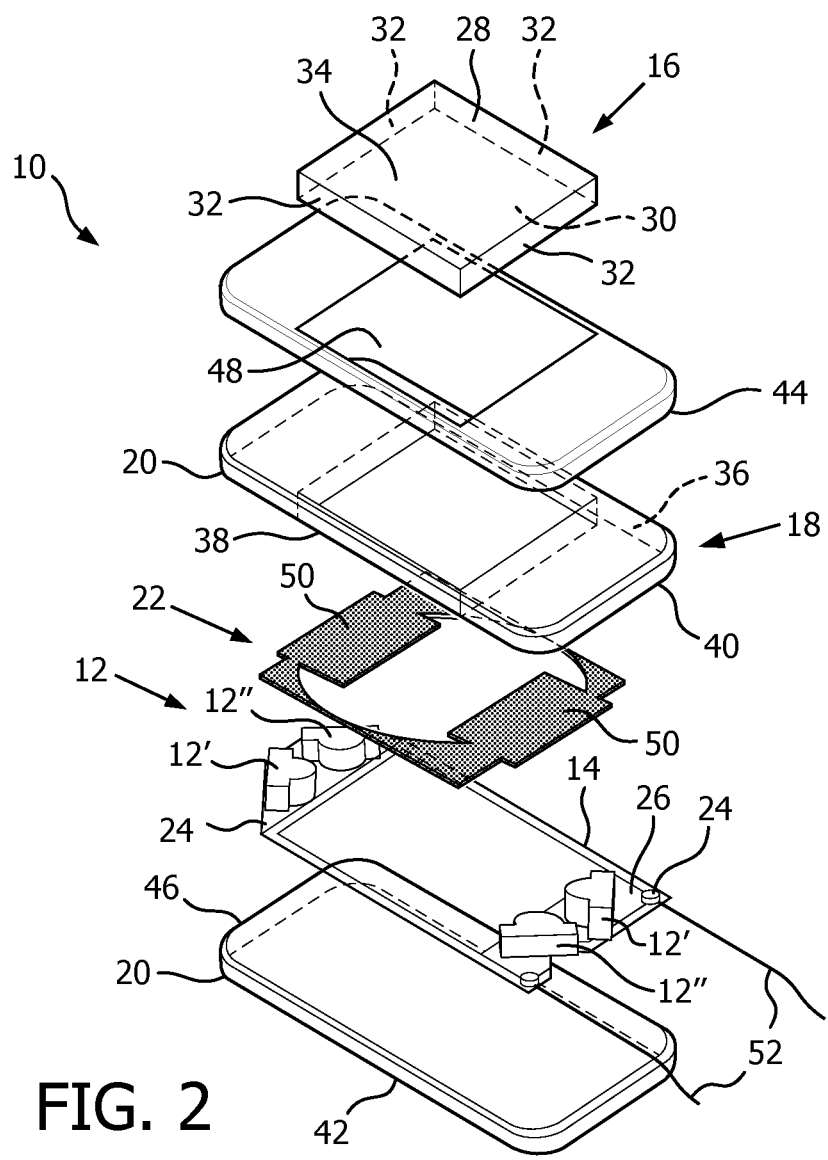
FIG. 2 is an exploded illustration of the optical source of FIG. 1 for use with a pulse oximeter.

With reference to FIG. 2, the optical source 10 of one embodiment includes at least one light source 12, a set of electronics 14, a flexible photodistributor 16, a flexible light-conducting sheet 18, a flexible housing 20, and a flexible light-absorbing material 22. The at least one light source 12 is configured to emit red light and infrared light. In one example, the at least one light source 12 can include at least one pair of LEDs with a first LED 12' configured to emit red light, and a second LED 12" configured to emit infrared light. As shown in FIG. 2, the at least one light source 12 includes two pairs of first LEDs 12' and second LEDs 12". It will be appreciated that the optical source 10 can include an equal number of first LEDS 12' and second LEDs 12". The first and second LEDs 12' and 12" in the illustrated embodiment are arranged in a substantially rectangular configuration. However, the first and second LEDs 12' and 12" can be arranged in a different configuration (e.g., circular).

The at least one light source 12 is operably connected to the set of electronics 14. The electronics 14 provide the electrical circuit components (e.g., a circuit board, contact wires, etc.) for the optical source 10. As shown in FIG. 2, the first LED 12' is positioned adjacent the second LED 12" at a first end 24 of the electronics 14. However, it will be appreciated that the first LED 12' can be positioned at the first end 24 of the electronics 14 and the second LED 12" can be positioned at a second end 26 of the electronics. The electronics 14 comprise an electronic circuit that is made of a flexible material (e.g., polyether, ether ketone, polyimide, transparent conductive polyester, a thin metal, etc.), thereby allowing the optical source 10 to fit to a curvature of the target tissue.

The flexible photodistributor 16 is configured to transmit and scatter each of the red light and the infrared light emitted from the at least one light source 12 towards the target tissue. The photodistributor 16 outcouples emitted red and infrared light from the at least one light source 12 as a homogeneous source of diffuse light, as described in more detail below. The photodistributor 16 has a light-emitting surface 28, a partially reflective surface 30, and at least one light-transmissive surface 32, for example, that is optically connected with the light-conducting sheet 18. Reflective particles 34 (e.g., TiO$_2$ particles) are suspended in the photodistributor 16. The reflective particles 34 can be microparticles or nanoparticles. For example, each reflective particle 34 can have a diameter ranging from about 0.2 microns to about 10 microns. In one example, the photodistributor 16 can be configured such that the reflective particles 34 are spatially varied with a higher density farther from the at least one light source 12 and a lower density closer to the at least one light source, forming a light-reflecting gradient, thereby creating a light distribution from the light-emitting surface 28 that has a selected homogeneity.

The photodistributor 16 has a thickness ranging from about 10 microns to about 2 millimeters. In one example, the photodistributor 16 has a thickness of about 1.0 millimeter. The photodistributor 16 has a surface area of about 1 cm$^2$; although the photodistributor can have a surface area of about 1 mm$^2$. The photodistributor 16 is illustrated as square; however, other shapes are possible (e.g., rectangular, circular, elliptical; n-sided polygonal, etc.). In some examples, the photodistributor 16 can have a tapered configuration, thereby increasing the homogeneity of the out-coupled light. In an alternative embodiment, the partially reflective layer 30 can be roughened to include an array of holes or dimples that are filled with an elastomeric material with a different refractive index than the material of the light-conducting sheet 18 (e.g., silicone) to achieve a homogeneous optical coupling.

The light-conducting sheet 18 is configured to conduct the red light and the infrared light emitted from the at least one light source 12 and function as a light guide between the at least one light source 12 and the photodistributor 16. The light-conducting sheet 18 is made from an elastomer (e.g., silicone). The light-conducting sheet 18 is molded around the at least one light source 12 and the electronics 14 such that the at least one light source and the electronics are immersed within the light-conducting sheet. As shown in FIG. 2, the light-conducting sheet 18 completely encloses the at least one light source 12 and the electronics 14. In one example, the photodistributor 16 and the light-conducting sheet 18 are two separate elements, in which the light-conducting sheet 18 is optically coupled to abutting edges of the photodistributor 16. In another example, the photodistributor 16 and the light-conducting sheet 18 are integrally formed together. In some instances, an optical coupling gel (not shown) is used to improve the optical coupling with the target tissue. Once molded, the first end 26 of the electronics 14 is encapsulated in a first end 38 of the light-conducting sheet 18, and the second end 28 of the electronics is encapsulated in a second end 40 of the light-conducting sheet. The light-conducting sheet 18 has a thickness that is about the same as the photodistributor 16. It will be appreciated that the thickness of the light-conducting sheet 18 can be varied to increase the homogeneity of the out-coupled light from the photodistributor 16. For example, the thickness of the light-conducting sheet 18 can be decreased at one or both of the first and second ends 38 and 40 thereof adjacent the at least one light source 12.

The flexible housing 20 is configured to hold and support the at least one light source 12, the electronics 14, the photodistributor 16, the light-conducting sheet 18, and the light-absorbing material 22. The light-conducting sheet 18 is covered with a white cover material 36 (e.g., silicone with high density TiO$_2$ nanoparticles) that reflects (i.e., blocks) the emitted red and infrared light. The white cover material 36 is also opaque to ensure that red and infrared light are scattered into a direction of the photodistributor 16 from which light is scattered homogeneously towards the target tissue. In one example, the white cover material 36 blocks any direct light path from the at least one light source 12 to the target tissue, thereby increasing the geometric homogeneity of the optical source 10. By keeping the emitted red and infrared light within the light-conducting sheet 18 until transmission into the photodistributor 16, the out-coupled light from the light-emitting surface 28 is homogeneous.

The housing 20 includes a base 42 and a complementary cover 44. The base 42 and the cover 44 are each made of a flexible, opaque elastomeric material (e.g., silicone with high density TiO$_2$ nanoparticles) for positioning the optical source 10 adjacent a curved target tissue. The base 42 and the cover 44 have a length of about 2 cm and a width of about 1 cm. It will be appreciated that the base 42 and the cover 44 can have any suitable dimensions for positioning the optical source 10 adjacent a narrow and/or curved target tissue. The base 42 includes a sidewall 46 extending around a perimeter thereof. The sidewall 46 encloses the light-conducting sheet 18. The cover 44 includes an opening or outlet 48. The opening 48 has a length and a width that corresponds to the length and the width of the photodistributor 16. The housing 20 has a reflective interior surface to reflect red and infrared light back into the light-conducting sheet 18 and the photodetector 16. In one embodiment, the housing 20 is a thin coating layer, such as foil or paint.

The light-absorbing material 22 is configured to absorb at least a portion of the scattered red light and at least a portion of the scattered infrared light. The light-absorbing material 22 is made from a flexible, material that absorbs both red and infrared light, (e.g., black). The light-absorbing material 22 abuts a portion of the lower surfaces of the photodistributor 16 and the light-conducting sheet 18. The light-absorbing material 22 is shaped to improve the uniformity of the red and infrared light emitted from the light-emitting surface 28 of the photodistributor 16. Because more light tends to be emitted adjacent the edges and in regions closer to the at least one light source 12, the light-absorbing material 22 substantially surrounds a perimeter of the photodistributor 16. The light-absorbing material 22 has at least one enlarged area 50 adjacent the at least one light source 12 for absorbing at least a portion of the red and infrared light emitted therefrom. The light-conducting sheet 18 can be molded to the light-absorbing material 22. Alternatively, the cover 44 can be colored (e.g., painted) in the area under the photodistributor 16 and adjacent edges of the light-conducting sheet 18. In another embodiment, the under sides of the photodistributor 16 and the light-conducting sheet 18 are selectively darkened or impregnated with a pattern of a light-absorbing material or particles.

Figure 3:
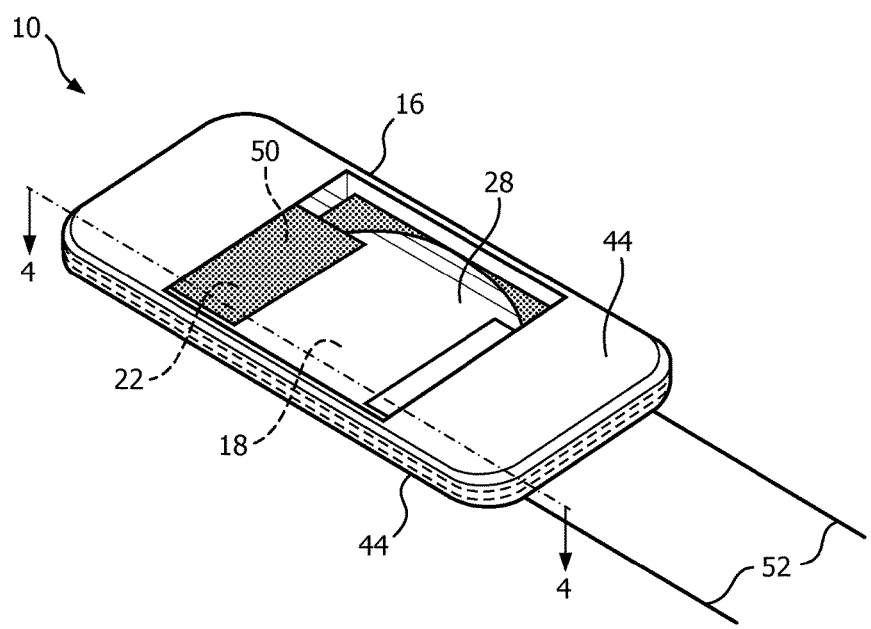
FIG. 3 is a perspective view of the optical source of FIG. 2 in an assembled configuration.

With reference to FIG. 3, assembly of the optical source 10 will now be described. One or more lead wires 52 are connected to the electronics 14. The at least one light source 12 is operably connected to the electronics 14 (e.g., by welding or soldering). The light-conducting sheet 18 is molded around the at least one light source 12, the electronics 14, at least a portion of the photodistributor 16, and the light-absorbing material 22. In one embodiment, the light-conducting sheet 18 is placed within the base portion 42 of the housing 20 and the cover 44 is then engaged with the base 42. In one example, the cover 44 is snap-fit with the base 42. In another example, the cover 44 and the base 42 are connected together by clips, magnets, hooks, and the like. In another embodiment, the base 42 and the cover 44 are a unitary coating layer. When the cover 44 is connected to the base 42, the opening 48 surrounds a perimeter of the light-emitting surface 28. In one example, the light-emitting surface 28 and the cover 44 cooperate to form a planar surface of the optical source 10. In another embodiment, the light-conducting sheet 18 is formed with an opening (not shown) for the photodistributor 16 and then the photodistributor is inserted with an optical coupling gel (not shown) or other coupling agent in the opening.

Once assembled, the optical source 10 in one embodiment has a length of about 2 cm, a width of about 1 cm, and a thickness of about 0.5-1 mm. The small thickness of the optical source 10 advantageously allows the optical source to be positioned within a narrow target tissue. It will be appreciated that the dimensions of the optical source 10 can be altered so that the optical source can be positioned in any other desired target tissue. In some instances, the opening 48 is centrally positioned in the cover 44. For example, the width of the opening 48 spans the width of the cover 44, and the length of the opening divides the cover into two equal opaque portions. It will be appreciated that the opening 48 can be positioned offset from the center of the cover 44. In another embodiment, the photodistributor 16 and the light-conducting sheet 18 are molded as a unitary construction. The reflective particles 34 are preferentially disposed away from the at least one light source 12 and adjacent a center of the opening 48.

The optical source 10 also has a high degree of flexibility. Advantageously, the electronics 14, the photodistributor 16, the light-conducting sheet 18, the housing 20, and the light-absorbing material 20 are made from an elastomeric material with a low degrees of stiffness and hardness (e.g., silicone); although another elastomeric material can be used. The flexibility of the optical source 10 allows the optical source to conform to any shape or contour of the human body it encounters, thereby ensuring optimal contact with the target tissue while homogenizing the contact pressure with the target tissue. A stiffness of 0.005 N/mm to 0.5 N/mm, measured over a span of about 15 millimeters, produces good results. The stiffness can be tailored by the choice of silicones and the thickness of the flexible electronic structure. In addition, the softness of the optical source 10 reduces the contact pressure on the target tissue, thereby increasing the comfort of the patient.

Figure 4:
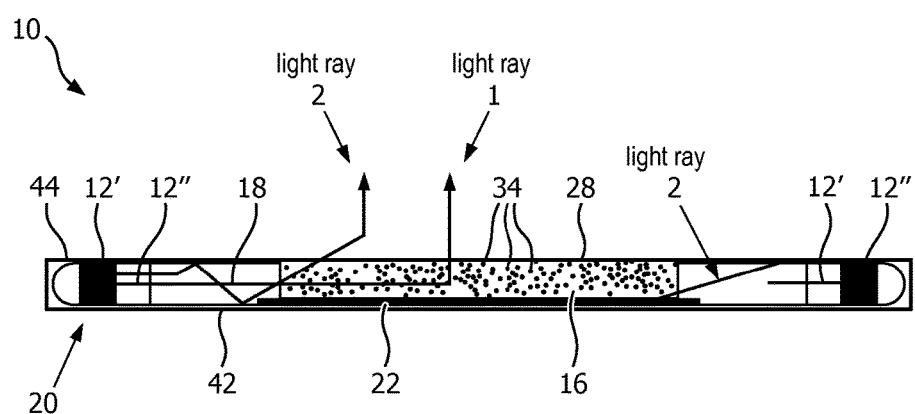
FIG. 4 is a cross-sectional view taken along Line 4-4 in FIG. 3.

With reference to FIG. 4, the optical source 10 is configured to direct light into a target tissue. The light-conducting sheet 18 is completely enclosed within the housing 20. The photodistributor 16 is substantially centered within the housing 20. The light-emitting surface 28 of the photodistributor 16 is substantially planar with a top surface of the cover 44. A first pair of including a first LED 12' and a second LED 12" are positioned at the first end 40 of the housing 20 and a second pair including a first LED 12' and a second LED 12" are positioned at the second end 42 of the housing. The light-conducting sheet 18 that encases first LED 12' is formed between the LEDs and the photodistributor 16.

When red and infrared light are emitted from the first and second LEDs 12' and 12", the light-conducting sheet 18 generally direct the light in a light-emitting direction that is substantially parallel to the light-emitting surface 28 (shown as light ray 1). As shown in FIG. 4, the light-emitting direction is a horizontal direction. At least a portion of the emitted red light and at least a portion of the emitted infrared light contact the light-conducting sheet 18. Upon contact, the light-conducting sheet 18 generally deflects the light away from the housing 20 and substantially into the light-emitting direction (shown as light ray 2). A portion of the red light and a portion of the infrared light are absorbed by the light-absorbing material 22 (shown as light ray 3). For example, the light-absorbing material 22 is positioned below the photodistributor 16 so that a homogeneous light stream is emitted from the light-emitting surface 28. The absorbed light by the light-absorbing material 22 does not contact the light-transmissive surfaces 32 of the photodistributor 16. The portions of the red light and the infrared light that are not absorbed contact the light-transmissive surfaces 32 and enter the photodistributor 16 (e.g., light rays 1 and 2). It will be appreciated that a portion of the light received by the photodistributor 16 has been deflected by the light-conducting sheet 18. The light is received by the thin multiple light-transmissive surfaces 32 to illuminate the photodistributor 16. The light received by the photodistributor 16 contacts the reflective particles 34 located therewithin. The reflective particles 34 redirect the light in an outcoupling direction that is substantially perpendicular to the light-emitting direction. As shown in FIG. 4, the outcoupling direction is a vertical direction. The red light and infrared light are outcoupled towards the target tissue for receipt by the light-receiving device 11 of the pulse oximeter 1 (see FIG. 1). Advantageously, the perpendicular change in direction of the red light and the infrared light increases the homogeneity of the outcoupled light towards the target tissue.

With reference to FIGS. 5A-5D, an optical source 54 for use with a light-receiving structure (not shown) of a pulse oximeter is provided for measuring information indicative of a patient's pulse rate and SpO$_2$. Unless specified below, elements of the optical source 54 are configured substantially similar to the elements of the optical source 10 that are described above. Repeated description of common elements between the optical source 10 and the optical source 54 are omitted for conciseness.

The optical source 54 includes at least one light source 56, a light-conducting sheet 58, a coating layer 60, and an outlet or opening 62. In one example, the at least one light source 56 can include at least one pair of optical fibers with a first optical fiber 56' configured to emit red light, and a second optical fiber 56" configured to emit infrared light. Alternatively, the at least one light source 56 can be configured as a single optical fiber configured to emit each of red light and infrared light. As shown in FIGS. 5A and 5B, the at least one light source 56 includes one pair of a first optical fiber 56' and second optical fiber 56". It will be appreciated that the optical source 54 includes an equal number of first optical fibers 56' and second optical fibers 56". The optical fibers 56' and 56" include roughened portions 64 to emit red and infrared light towards the outlet 62. For example, the roughened portions 64 are formed by abrasive blasting. The degree of roughness of the roughened portions is increased towards a tip of the optical fibers 56' and 56" to ensure a homogenous light intensity along the length of the optical fibers. With reference to FIGS. 5C and 5D, the optical source 54 includes a single optical fiber 56' with roughened portions 64 that is led through a portion of the photodistributor 16. By leading the optical fiber 56' through the photodistributor 58, the homogeneity of the out-coupled light is increased.

Referring back to FIGS. 5A and 5B, the light-conducting sheet 58 is molded around a portion of the optical fibers 56' and 56" so that the optical fibers are embedded into a portion of the light-conducting sheet. In this embodiment, the photodistributor 16 described above is integrally formed with the light-conducting sheet 58. In other words, the light-conducting sheet 58 includes the characteristics of the photodistributor 16 and the light-emitting sheet 58 (described above). Preferably, the light-conducting sheet 58, like the photodistributor 16, has a stiffness less than 0.5 N/mm, measured over a span of about 15 millimeters. As shown in FIGS. 5A and 5B, the optical fibers 56' and 56" are disposed at a first end 66 of the light-conducting sheet 58. The light-conducting sheet 58 is formed from an elastomeric material having a low rigidness value (e.g., silicone), thereby providing the optical source 54 with a high level of flexibility. The light-conducting sheet 58 is transparent for guiding emitted red and infrared light towards the target tissue. The light-conducting sheet 58 has a length of about 2 cm and a width of about 1 cm. The light-conducting sheet 58 has a thickness of about 10 microns to about 2 millimeters. The thickness of the light-conducting sheet 58 can be varied (e.g., at the location of the at least one light source 56) to increase the intensity of the outcoupled light. In an alternative embodiment, the light-conducting sheet 58 can include a diffusing medium, such as the reflective particles 34, immersed therein for homogenous outcoupling of the emitted red and infrared light.

The light-conducting sheet 58 is coated with the coating layer 60 that is made from a non-transparent diffusing or reflective material and can include reflective particles (e.g., $TiO_2$) for diffusely reflecting the emitted red light and the emitted infrared light. The coating layer 60 substantially surrounds the light-conducting sheet 58, except for a portion of the light-conducting sheet that includes the outlet 62. Stated another way, the outlet 62 is defined as the portion of the light-conducting sheet 58 that is not surrounded by the coating layer 60.

The outlet 62 is configured to discharge the emitted light into the target tissue. As shown in FIGS. 5A and 5B, the outlet 62 is located at an opposing second end 68 of the light-conducting sheet 58. The outlet 62 is circular; however, the outlet can have any desired shape. The outlet 62 can have, for example, a diameter of about 9 mm. However, it will be appreciated that the outlet 62 can have any suitable dimensions for reflecting light from the photodistributor towards the target tissue.

When red light and infrared light are emitted from the optical fibers 56' and 56", the emitted light is directed towards the outlet 62 in a light-emitting direction (illustrated in FIGS. 5A and 5B as the vertical direction). A portion of the emitted light contacts the coating layer 60, which diffusely reflects the light generally into the light-emitting direction. When the emitted red and infrared light reaches the outlet 62, the coating layer 60 is not present to reflect the light. Consequently, the light is emitted out of the light-conducting sheet 58 into the abutting target tissue and the light-receiving device (not shown).

Figure 6:
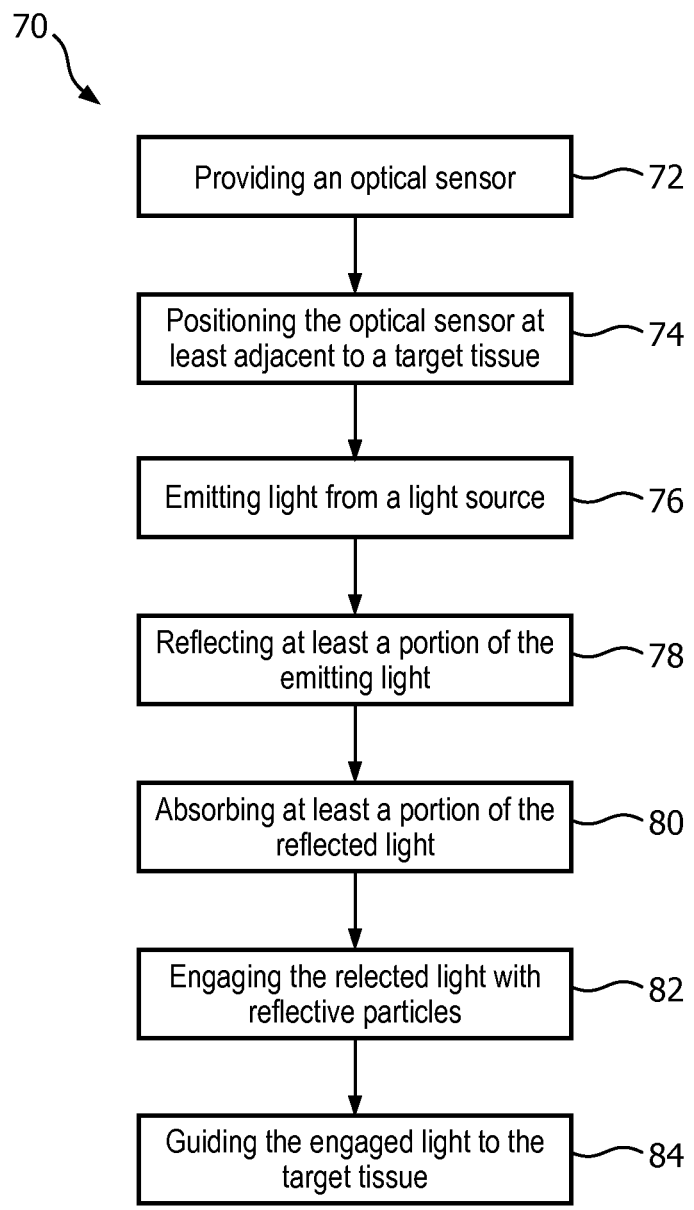
FIG. 6 is an exemplary flowchart illustrating the guiding of light from the optical source to a target tissue.

With reference to FIG. 6, a method 70 of guiding light towards a target tissue of a patient is described. The method 70 comprises the steps of: providing an optical source (Step 72); positioning the optical source at least adjacent to, and in contact with, a target tissue (Step 74); emitting light from a light source (Step 76); reflecting at least a portion of the emitted light (Step 78); absorbing at least a portion of the reflected light (Step 80); engaging the reflected light with reflective particles (Step 82); and discharging the light into the target tissue (Step 84).

At Step 72, an optical source 10, 54 is provided. The optical source 10, 54 is configured and assembled as described above. In one example, the at least one light source 12,56, the photodistributor 16 the light-conducting sheet 18, 58, and the housing 20 or the coating layer 60 are each formed from an elastomeric material having a low rigidness value, thereby providing the device with a high level of flexibility. In another example, the photodistributor 16 has an area that conforms to the target tissue (e.g., ranging from approximately 1 $mm^2$ to approximately 1 $cm^2$), and includes a thickness of approximately 1 millimeter (e.g., —approximately 10 microns to approximately 2 millimeters).

At Step 74, the optical source 10, 54 is pressed into contact with a target tissue (e.g., on a portion of the septum). However, it will be appreciated that the optical source 10, 54 can be positioned on or adjacent to any suitable target tissue. In some instances, a positioning device (not shown), such as a balloon, a clip, or an adhesive, can be engaged with the optical source 10, 54 to at least temporarily position the optical source against the target tissue.

At Step 76, light is emitted from the at least one light source 12, 56. The at least one light source 12 includes a first LED 12' (or a first optical fiber 56') that emits red light and a second LED 12" (or a second optical fiber 56") that emits infrared light. The at least one light source 12, 56 is mounted within the housing 20 (or the coating layer 60) such that some red and infrared light emitted therefrom travels in a light-emitting direction that is substantially parallel to the light-emitting surface 28 of the photodistributor 16. The emitted red and infrared light is guided towards the photodistributor 16 by the light-conducting sheet 18, 58.

At Step 78, at least a portion of the emitted red light and at least a portion of the emitted infrared light are reflected by the light-conducting sheet 18, 58. The white cover material 36 of the light-conducting sheet 18, 58 prevents passage of the emitted light out of the housing 20 (or the coating layer 60). Rather, the light-conducting sheet 18, 58 reflects the emitted light away from the housing 20 (or the coating layer 60). The emitted light continues to move generally towards the photodistributor 16 after reflection of the light by the light-conducting sheet 18, 58.

At Step 80, at least a portion of the emitted light is absorbed. In one example, the light-absorbing material 22 absorbs emitted light regardless of whether the absorbed light has been reflected by the light-conducting sheet 18, 58. The light-absorbing material 22 absorbs at least a portion of the emitted light to provide a homogeneous light stream out of the light-emitting surface 28 of the photodistributor 16.

At Step 82, a portion of the light is received by the photodistributor 16. The portion of the emitted light that is not absorbed by the light-absorbing material 22 engages the light-transmissive surfaces 32 of the photodistributor 16. It will be appreciated that a portion of the light received by the photodistributor 16 has been deflected by the light-conducting sheet 18, 58. The light is received by the thin multiple light-contacting surfaces 32 to illuminate the photodistributor 16.

At Step 84, the light is deflected towards the target tissue. Once the light has been received by the photodistributor 16, the light interacts with the reflective particles 34 contained within the photodistributor. The reflective particles 34 deflect the light in an outcoupling direction towards the target tissue. The outcoupling direction of the red light and the infrared light is perpendicular to light-emitting direction. Once the light is guided to the target tissue, the light is received by a light-receiving structure (not shown), thereby allowing a pulse oximeter to measure information indicative of a patient's pulse rate and $SpO_2$.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An optical source for guiding light to a target of a patient, the optical source comprising:
    at least one light source configured to emit red light and infrared light, the at least one light source being embedded within a flexible light-conducting sheet;
    a flexible photodistributor spaced from the at least one light source, the photodistributor including a light-emitting surface and at least one light-receiving surface optically coupled to the light-conducting sheet, the photodistributor being configured to discharge at least a portion of the emitted red light and at least a portion of the emitted infrared light into a target; and
    a housing configured to encase the at least one light source, the photodistributor, and the light-conducting sheet, the housing defining an opening, the housing being configured to reflect light emitted from the at least one light source, the photodistributor being separately formed from the light-emitting sheet.

2. The optical source according to claim 1, further including at least one suspended reflective particle disposed within the photodistributor, a density of the reflective particles being configured such that a light distribution from the light-emitting surface has a selected homogeneity.

3. The optical source according to claim 1, further comprising an electronics set operably connected to the at least one light source, the light-conducting sheet being molded around at least a portion of the electronics set.

4. The optical source according to claim 1, wherein the light-conducting sheet and the housing are each formed from a flexible elastomeric material, thereby providing the optical source with a high level of flexibility.

5. The optical source according to claim 1, further comprising a light-absorbing material disposed adjacent a back side of at least one of the photodistributor and the light-conducting sheet, the light-absorbing material being distributed to render the emitted light more uniform.

6. The optical source according to claim 5, wherein the housing includes:
    a base for supporting the light-conducting sheet; and
    a cover that overlies at least a portion of the light-conducting sheet, the cover including the opening, which is configured to receive the light-emitting surface of the photodistributor;
    wherein the light-absorbing material is positioned on the base such that the light absorbing material is disposed between at least a portion of the base and at least a portion of the light-conducting sheet.

7. The optical source according to claim 1, wherein the light-emitting surface of the photodistributor light-emitting surface has an area ranging from approximately 1 mm² to approximately 1 cm².

8. The optical source according to claim 1, wherein the photodistributor has a thickness ranging from approximately 10 microns to approximately 10 millimeters, the photodistributor having a tapered thickness, thereby increasing the homogeneity from the light-emitting surface.

9. The optical source according to claim 1, wherein the at least one light source comprises at least one pair of LEDs, the at least one pair of LEDs including at least one LED configured to emit red light and at least one LED configured to emit infrared light.

10. The optical source according to claim 1, wherein the at least one light source comprises at least one pair of optical fibers, the at least one pair of optical fibers including at least one optical fiber configured to emit red light and at least one optical fiber configured to emit infrared light.

11. The optical source according to claim 1, wherein the at least one light source comprises a single optical fiber positioned through at least one of the light-emitting sheet and the photodistributor.

12. A method for lighting a target with red and infrared light, the method comprising:
    positioning an optical source at least adjacent to the target;
    emitting each of red light and infrared light from at least one light source;
    guiding at least a portion of the red light and at least a portion of the infrared light along a flexible light-conducting sheet; and
    directing at least a portion of the red light and at least a portion of the infrared light into the target via a flexible light-emitting surface that abuts at least a portion of the target;
    reflecting at least a portion of the red light and at least a portion of the infrared light via at least one reflective particle disposed within a photodistributor; and
    absorbing at least a portion of the red light and at least a portion of the infrared light via a light-absorbing material disposed substantially surrounding a perimeter of a photodistributor.

13. The method according to claim 12, further comprising:
    directing a homogenous light beam out of the light-emitting surface.

14. An optical source for guiding light to a target of a patient, the optical source comprising:
    at least one light source configured to emit red light and infrared light;
    a light-conducting sheet molded around at least a portion of the at least one light source, the light-conducting sheet being configured to guide at least a portion of emitted red light and at least a portion of emitted infrared light;
    a coating layer disposed on at least a portion of the light-conducting sheet, the coating layer being configured to reflect at least a portion of the emitted red light and at least a portion of the emitted infrared light and retain the emitted red light and infrared light in the light-conducting sheet; and
    an outlet disposed on a portion of the light-conducting sheet that is free from engagement with the coating layer, the outlet being surrounded by at least a portion of the coating layer, the outlet being configured to emit red light and infrared light towards a target.

15. The optical source according to claim 14, further including at least one suspended reflective particle disposed within the light-conducting sheet, a density of the reflective particles being distributed inhomogeneously such that a light distribution from the light-conducting sheet is spatially homogenous.

16. The optical source according to claim 14, further comprising a light-absorbing material adjacent at least one of the coating layer and the light-conducting sheet, the light-absorbing material being distributed to render the emitted light more uniform.

17. The optical source according to claim 14, wherein the light-conducting sheet has a thickness of less than 1 millimeter.

18. The optical source according to claim 14, wherein the at least one light source comprises at least one pair of optical fibers, the at least one pair of optical fibers including at least one optical fiber configured to emit red light and at least one optical fiber configured to emit infrared light.

* * * * *